United States Patent [19]

Webber

[11] Patent Number: 5,214,686

[45] Date of Patent: May 25, 1993

[54] THREE-DIMENSIONAL PANORAMIC DENTAL RADIOGRAPHY METHOD AND APPARATUS WHICH AVOIDS THE SUBJECT'S SPINE

[75] Inventor: Richard L. Webber, Winston-Salem, N.C.

[73] Assignee: Wake Forest University, Winston-Salem, N.C.

[21] Appl. No.: 808,181

[22] Filed: Dec. 13, 1991

[51] Int. Cl.$^5$ .............................................. A61B 6/14
[52] U.S. Cl. ...................................... 378/38; 378/39; 378/40; 378/98; 378/99; 378/147
[58] Field of Search .................... 378/38, 14, 39, 40.4, 378/147, 148, 149, 204, 98, 99

[56] References Cited

U.S. PATENT DOCUMENTS

| | | | |
|---|---|---|---|
| 4,188,541 | 1/1980 | Hounsfield | 378/14 |
| 4,239,971 | 12/1980 | Cushman | 378/39 |
| 4,259,582 | 3/1981 | Albert | 378/99 |
| 4,264,824 | 4/1981 | Tosswill | 378/146 |
| 4,304,999 | 12/1981 | Richey et al. | 378/4 |
| 4,315,157 | 2/1982 | Barnes | 378/10 |
| 4,481,650 | 11/1984 | Kinanen | 378/7 |
| 4,589,122 | 5/1986 | Nieminen | 378/39 |
| 4,709,382 | 11/1987 | Sones | 378/146 |
| 4,731,807 | 3/1988 | Plessis et al. | 378/146 |
| 4,741,007 | 4/1988 | Virta et al. | 378/39 |
| 4,750,196 | 6/1988 | Harding | 378/87 |
| 4,783,793 | 11/1988 | Virta et al. | 378/39 |
| 4,788,699 | 11/1988 | Dobert et al. | 378/38 |
| 4,817,119 | 3/1989 | Ledley et al. | 378/4 |
| 4,847,881 | 7/1989 | Heubeck | 378/38 |
| 4,878,234 | 10/1989 | Pfeiffer et al. | 378/40 |
| 4,907,251 | 3/1990 | Mork et al. | 378/39 |
| 4,991,190 | 2/1991 | Mori | 378/9 |
| 5,018,177 | 5/1991 | McDavid et al. | 378/39 |
| 5,093,852 | 3/1992 | Nishikawa et al. | 378/39 |

FOREIGN PATENT DOCUMENTS 57-67847 4/1982 Japan .

OTHER PUBLICATIONS

Tomosynthesis: A Three-Dimensional Radiographic Imaging Technique, D. G. Grant, IEEE Transactions on Bio-Medical Engineering, vol. BME-19, No. 1, Jan., 1972, pp. 20–28.

Computerized Tomosynthesis of Dental Tissues, A. J. Groenhuis et al., *Dental Radiology*, Oral Surg., vol. 56, No. 2, Aug., 1983, pp. 206–214.

A Prototype Digital Tomographic X-Ray System for Dental Applications, R. A. J. Groenhuis et al., IEEE International Symposium on Medical Images and Icons, Jul. 24–27, 1984, Arlington, Va., pp. 218–221.

Restoration of Digital Multiplane Tomosynthesis by a Constrained Iteration Method, U. E. Ruttimann et al., IEEE Transactions on Medical Imaging, vol. MI-3, No. 3, Sep. 1984, pp. 141–148.

Synthesis of Arbitrary X-Ray Projections from a Finite Number of Existing Projections, SPIE vol. 535-application of Optical Instrumentation in Medicine in XIII (1985) pp. 84–90.

Medical Image Reconstruction: Multiangular Sectional Roentgenography by Computer, R. M. Perry et al., NCAR Technical Note, NCAR-TN/STR-108, Aug., 1975, pp. 1–147.

*Primary Examiner*—David P. Porta
*Assistant Examiner*—Kim-Kwok Chu
*Attorney, Agent, or Firm*—Bell, Seltzer, Park & Gibson

[57] ABSTRACT

A panoramic dental radiography system projects multiple vertical, fan-shaped radiation beams through a subject's teeth and onto multiple detectors, with each fan-shaped beam avoiding the subject's spine. The radiographic source and radiographic detectors are rotated about a vertical axis, so that the detected radiation may be tomographically processed to produce a panoramic image of the teeth. The multiple vertical fan-shaped radiation beams are projected on either side of the spine, to reduce the radiographic dosage to the spine and to prevent the spine from blurring the panoramic radiograph. The resulting multiple projections can be tomosynthetically processed to produce a three-dimensional image of tissues of diagnostic interest, free of image artifacts produced by irradiation of the spine.

18 Claims, 7 Drawing Sheets

THREE-DIMENSIONAL PANORAMIC DENTAL RADIOGRAPHY METHOD AND APPARATUS WHICH AVOIDS THE SUBJECT'S SPINE

FIELD OF THE INVENTION

This invention relates to radiographic imaging and more particularly to dental radiographic imaging.

BACKGROUND OF THE INVENTION

Tomography is an analog imaging process which is widely used for radiographic imaging. In tomography, an x-ray beam source and an x-ray film are moved in predetermined directions relative to one another, such that the fulcrum of relative movement between the source and the film defines a region of interest. Since relative movement at the fulcrum is zero, this region is projected unchanged onto the film. The radiographic projections of all tissues lying outside this region move during exposure, so that they appear more or less blurred depending on their distance from the fulcrum. The amount of blur is directly proportional to their distance from the fulcrum. Accordingly, the region or fulcrum is often referred to as the "focal plane".

In summary, the tomographic process capitalizes on the angular disparity produced by relative motion between x-ray source and x-ray detector to selectively isolate a region, the location of which can be varied by controlling motion relative to the tissues of interest. In tomographic imaging, linear motion of the source and detectors may be used ("linear tomography") or circular motion of the source and detector may be used ("circular tomography"). Depending upon the diagnostic task, other more complex motions may be used, such as hypercycloidal motion ("hypercycloidal tomography").

A related but computationally distinct imaging process for obtaining tomographic "slices" is computed tomography. In computed tomography, the projection geometry is characterized by a fan-shaped x-ray beam which lies in the same plane as a detector. This geometry renders details in one focal plane independent from those in another focal plane, but at the expense of having the plane of the source and detector motion coincident with the focal plane.

Linear tomography has been used in dental radiography to obtain images of individual teeth or groups of teeth. Computed tomography also has been used in dental radiography to obtain a slice through a subject's head, parallel to the plane of the subject's teeth.

In the above description, and in the description to follow, reference is made to the "plane of the teeth", which is defined as the plane formed by the intersection of a subject's upper and lower teeth. This plane, which is parallel to the plane of the jaw, is typically a horizontal plane when the subject is in a normal upright (standing or sitting) position. Accordingly, the term "horizontal" will be used to refer to a direction parallel to the plane of the teeth, which is typically a horizontal plane. The term "vertical" will be used to refer to a direction perpendicular to the plane of the teeth, which is generally parallel to a subject's spine, and is vertical when the subject is in the typical upright position.

The process of tomography has been extended to digital tomosynthesis, which produces a series of discrete images taken from different positions as the x-ray source and detector move about a fixed fulcrum. Each discrete image corresponds to a different relative position of the source and film plane, rather than a single image produced continuously. In linear tomography and linear tomosynthesis the source and the detector move in a straight line about a fulcrum lying in the tissues which define the plane to be seen sharply in the reconstruction.

It has been shown that the tomosynthetic process is theoretically indistinguishable from the tomographic process, provided that the size of the smallest detail of interest can be specified and the number of discrete projections is sufficiently large. These processes are indistinguishable because they both operate by isolating a focal plane through a controlled blur as described above. However, tomosynthesis has an advantage over tomography, because simple manipulation of the radiographic intensity data obtained from the multiple images permits the position of the focal plane to be adjusted after the fact. Accordingly, a computer can be used to selectively search through the multiple images and to render the image of a particular structure of interest in proper focus, irrespective of its location.

The theoretical and practical designs of a tomosynthetic x-ray system are well known to those having skill in the art, and are described, for example, in an article entitled *Tomosynthesis: Three-Dimensional Radiographic Imaging Technique* by D. G. Grant, published in the IEEE Transactions on Bio-Medical Engineering, Vol. BME-19, No. 1, Jan., 1972, pp. 20-28. The present inventor likewise has coauthored a number of articles describing computer tomosynthesis. See the articles entitled *Computerized Tomosynthesis of Dental Tissues*, coauthored with Groenhuis and Ruttimann, published in Oral Surgery, Vol. 56, No. 2, pp. 206-214, Aug., 1983; *A Prototype Digital Tomographic X-Ray System For Dental Applications* coauthored with Groenhuis and Ruttimann, published in the IEEE International Symposium on Medical Images and Icons, Jul. 24-27, 1984, pp. 218-221; *Restoration of Digital Multiplane Tomosynthesis By a Constrained Iteration Method*, coauthored with Ruttimann and Groenhuis, published in the IEEE Transactions on Medical Imaging, Vol. MI-3 Sep., 1984, pp. 141-148; and *Synthesis of Arbitrary X-ray Projections From a Finite Number of Existing Projections* coauthored with Ruttimann, Groenhuis and Edholm, published in Society of Photo-optical Instrumentation of Engineers, Application of Optical Instrumentation in Medicine XIII, Vol. 535, pp. 84-90, 1985.

Panoramic dental radiography is also widely used for dental imaging. In contrast with conventional single tooth exposures, panoramic dental radiography attempts to "unwrap" the curved jaw and teeth into a flat panoramic image. In other words, panoramic dental radiography is a unique imaging technique for showing all of the teeth and related dental tissues on a single exposed film in one "panoramic sweep". It results from a system that dynamically alters the swept projection using an exposure geometry that establishes foci that are different in the horizontal and vertical directions.

Panoramic radiography resembles linear tomography to the extent that it produces images characterized by a region of sharp focus that is controlled by the motion of the x-ray beam and the x-ray film relative to the irradiated tissues. However, unlike tomography the image is produced from a fan-shaped x-ray beam which scans across a moving film as the source of radiation moves in a complicated path around the patient's head. The result is an image which shows relatively sharp images of the teeth unwrapped from the dental arch, but buried in blurred images of other tissues laying further away from the region of interest.

Panoramic radiography involves horizontal rotation of a single fan-shaped x-ray beam and an x-ray detector, such as a photographic plate, about an axis which is generally parallel to the subject's spine and orthogonal to the plane of the teeth. The single fan-shaped beam is a vertical beam, which extends orthogonal to the plane of the teeth. In contrast with tomography, the x-ray film is also moved relative to the x-ray beam, at a constant velocity which is synchronized to the rotation of the x-ray source and film. In the limit (i.e. when the fan-shaped beam is infinitely thin), this movement places the effective tomographic fulcrum at infinity, thus precluding all tomographic blur. On the other hand, by increasing the thickness of the fan-shaped beam, it is possible to introduce more and more tomographic blurring into the resulting panoramic radiograph, to render sharp only the image of structures lying a focal plane determined by the relative movement of the source and detector.

In summary, panoramic radiography sweeps an extended film with a modulated fan-shaped beam to produce an extended image with a lateral extent and projective attributes impossible to produce directly from a single exposure. The degree to which the unwanted out-of-plane structures are tomographically blurred is determined by the horizontal width of the fan beam as it is projected onto the moving film, and by the relative movement of the x-ray source and projected tissues relative to the plane of the fulcrum. Taken together, these processes result in an imaging system that permits the teeth to be viewed tomographically in spite of the fact that they lie in an arched arrangement inside the head.

Panoramic radiography systems are described in U.S Pat. Nos. 4,589,122 to Nieminen entitled *Panoramic Tomography X-ray Apparatus;* 4,783,793 to Virta et al. entitled *X-ray Apparatus for Panoramic Tomography Including Control System;* 4,847,881 to Heubeck entitled *Dental X-ray Diagnostics Installation For Producing Panoramic Tomograms of the Jaw of a Patient;* and 4,878,234 to Pheiffer et al. entitled *Dental X-ray Diagnostics Installation for Producing Panorama Slice Exposures of the Jaw of a Patient.*

Although useful for producing panoramic images of a subject's teeth, known panoramic dental radiographic systems possess a number of shortcomings. For example, the usefulness of dental panoramic radiography depends greatly on the degree to which the structures of interest lie close to the focal plane. If the region of relative lack of blur is too wide, structures other than teeth and jaws also appear sharp, and obscure details of the structure of diagnostic interest. Hence, in order to prevent unwanted features from appearing clearly, tomographic blurring typically is adjusted to render only images quite near the focal plane in relative focus. Unfortunately, such a design makes the system highly sensitive to subject positioning. If the subject is not positioned properly, the dental structures of interest may not be present in the region of clear tomographic focus, so that the image of important diagnostic details becomes blurred.

A particular problem related to dental panoramic radiography stems from the fact that the images of unwanted structures outside the region of clear focus are only blurred, rather than being eliminated completely. Accordingly, a large diffuse structure is less influenced by the blurring process than a small, sharply delineated tissue detail. This is a particular problem in dental panoramic radiography because the vertical fan-shaped x-ray beam passes through the spine. The midline position of the spine has heretofore precluded x-ray projections which avoid the spine.

The need to pass an x-ray beam through the spine in a dental radiographic applications, produces two deleterious effects. First, it requires a higher x-ray dose than would otherwise be required, in order to provide sufficient x-ray density at the teeth after passing through the spine. Moreover, it produces a large massive blur on the x-ray film which often obscures structures of interest.

Yet another problem with conventional panoramic radiographic systems is the overlap of the teeth in the panoramic radiograph. This overlap takes place because the x-rays are not always directed between the proximal surfaces of the teeth. Accordingly, the interproximal regions of a number of teeth typically overlap in the panoramic radiograph, thereby obscuring necessary details.

It is known that multiple beams can be produced from a single x-ray source, using a suitable x-ray collimator. See U.S. Pat. No. 4,264,824 to Tosswill entitled *Far Field Imaging*, which describes a collimator for use in imaging far field sources, and U.S. Pat. No. 4,304,999 to Richey et al. entitled *Eccentric Source Collimator Assembly for Rotating Source CT Scanner*. Multiple beams, which may be produced by collimating a single x-ray source, may be used in multiple beam computer tomography as described in U.S. Pat. No. 4,315,157 to Barnes entitled *Multiple Beam Computed Tomography (CT) Scanner*. It is also known to use at least two fan-shaped beams having different energy spectra which are obtained from a single x-ray source to produce several negatives or exposures of a single area or zone, and to superpose these exposures, as described in U.S. Pat. No. 4,731,807 to Plessis et al. entitled *X-ray Examination Apparatus.*

Finally, it is also known to obtain panoramic dental x-ray images from multiple diverging fan-shaped beams, which extend orthogonal to the plane of the teeth, by synchronously rotating the fan-shaped beams, and corresponding detectors, about an axis orthogonal to the plane of the teeth. See U.S. Pat. No. 4,481,650 to Kinanen. Five vertical fan-shaped beams are used, with one beam being a centrally located beam which passes radiation through the subject's spine. The remaining beams are symmetrically arranged about the central beam.

In summary, known panoramic dental radiography techniques, which use single or multiple fan-shaped x-ray beams are highly position sensitive, include excessive overlap of interproximal areas of the teeth, require higher doses, and produce interpretive artifacts due to the effects of the spine.

SUMMARY OF THE INVENTION

It is therefore an object of the present invention to provide an improved panoramic dental radiography method and apparatus.

It is another object of the present invention to provide a panoramic dental radiography method and apparatus which reduces the effect of the spine on x-ray dose and image quality.

These and other objects are provided, according to the present invention, by simultaneously projecting a plurality of vertical (i.e. extending orthogonal to the plane of a subject's teeth) diverging, fan-shaped radiation beams through a subject's teeth, which each fan-shaped beam avoiding the subject's spine. The attenuated radiation which emerges through the teeth is detected, with the detected attenuated radiation being free of attenuation produced by the spine. The radiographic source and radiographic detector are synchronously rotated about a vertical axis (i.e. orthogonal to the plane of the subject's teeth), with each of the fan-shaped beams avoiding the spine during rotation thereof. The detected attenuated radiation produces multiple panoramic images of the teeth which are free of image artifacts produced by irradiation of the spine.

According to the invention, the plurality of diverging vertical fan-shaped radiation beams pass through a subject's head, with each of the fan-shaped beams avoiding the subject's spine. The fan-shaped beams pass on either side of the spine but no beam passes through the spine. Accordingly, image artifacts caused by irradiation of the spine are eliminated. Moreover, a reduced dosage results, because the primary x-ray beams need not pass through the spine. Finally, exposure of the radiosensitive marrow producing spine is eliminated.

The plurality of diverging vertical fan-shaped x-ray beams may be produced by a collimated x-ray source. A linear radiation detector, such as a vertical, linear Charge Coupled Device (CCD) array, may be positioned to intercept a respective one of the fan-shaped beams which emerge from the subject's head, with each of the beams avoiding the subject's spine. The signals detected by the detectors may be processed as conventional panoramic data to produce a panoramic image of the teeth. The images so produced have decreased sensitivity to subject positioning and reduced interproximal overlap compared to conventional panoramic images.

The images produced according to the invention may be thought of as being equivalent to that produced from a hypothetical two-step process:

1) a highly nonlinear warping transformation that opens the head from the back and flattens it out such that the teeth are oriented in a relatively straight line rather than bent into the arch-shaped configuration that they normally occupy, and
2) application of linear tomosynthesis to the resulting grossly distorted tissue mass. The desired tomosynthetic slices are produced from focal planes parallel to the now flattened plane containing the "unwrapped" teeth.

The invention produces reduced blurring without extreme sensitivity to subject position. The distortion and dosage effects of the spine are eliminated, and reduced interproximal overlap is provided. The invention may be practiced by modifying conventional digital tomosynthesis systems to provide multiple vertical fan-shaped beams which avoid the spine, and multiple vertical linear detector arrays, to obtain simultaneous acquisition of multiple panoramic projections, each produced at a different angle. Tomosynthetic processing may then be used to obtain three-dimensional information.

DESCRIPTION OF A PREFERRED EMBODIMENT

The present invention now will be described more fully hereinafter with reference to the accompanying drawings, in which a preferred embodiment of the invention is shown. This invention may, however, be embodied in many different forms and should not be construed as limited to the embodiment set forth herein; rather, this embodiment is provided so that this disclosure will be thorough and complete, and will fully convey the scope of the invention to those skilled in the art. Like numbers refer to like elements throughout.

Figure 1:
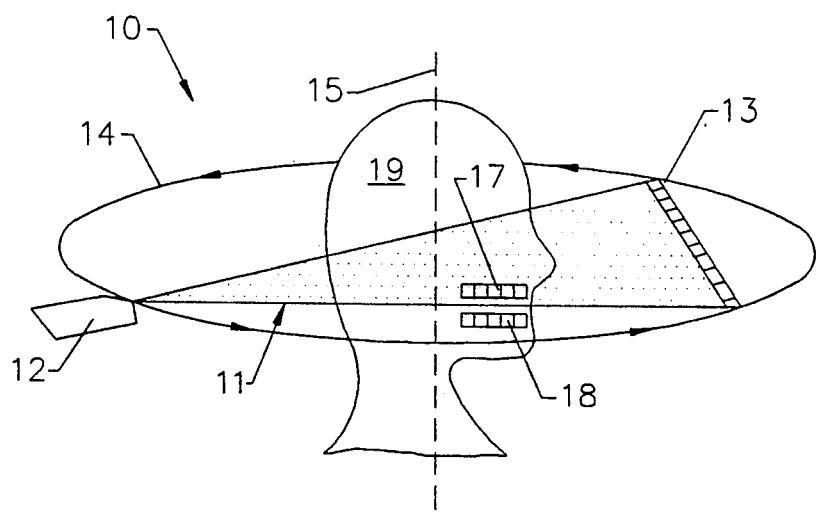
FIG. 1 schematically illustrates a conventional computed tomographic system.

Prior to describing the panoramic radiography method and apparatus of the present invention, a description of a computed tomography system will be provided, followed by a description of a conventional panoramic radiographic system. FIG. 1 schematically illustrates a computed tomography system, which is oriented to obtain a slice through the head, including the plane of the teeth. As shown, computed tomography system 10 projects a single, horizontal fan-shaped x-ray beam 11 from a source 12 to a linear detector array 13. The x-ray source 12 and virtual linear detector array 13 are rotated in a horizontal rotation path 14, without translational movement between the source 12 and the detector 13. Horizontal rotation typically takes place about a vertical axis 15 Which is centered near the spine of the subject 19.

In circular tomography, the detector array 13 would be replaced by an x-ray film cassette, and the rotation is typically a continuous rotation. In computed tomography, multiple discrete line integrals are produced, each corresponding to a different relative position of the source and detector, rather than a continuous tomographic reproduction.

Tomography and tomosynthesis both rely on the blurring of unwanted details which are outside the region of sharp focus. However, tomosynthesis possesses a unique advantage over tomography because simple manipulation of data obtained from the multiple images permits the position of the focal plane to be adjusted after the fact. In particular, a computer can be used to selectively search through multiple images and render the image of a particular structure of interest in proper focus, regardless of its particular location. Moreover, the projection geometry responsible for the blurs, at any distance from the focal plane, is known in advance. Accordingly, the exact nature of the blurring process produced by unwanted structures may be predicted with certainty. This means that deconvoluting algorithms may be used to further suppress blur resulting from structures lying outside the focal plane.

Figure 2:
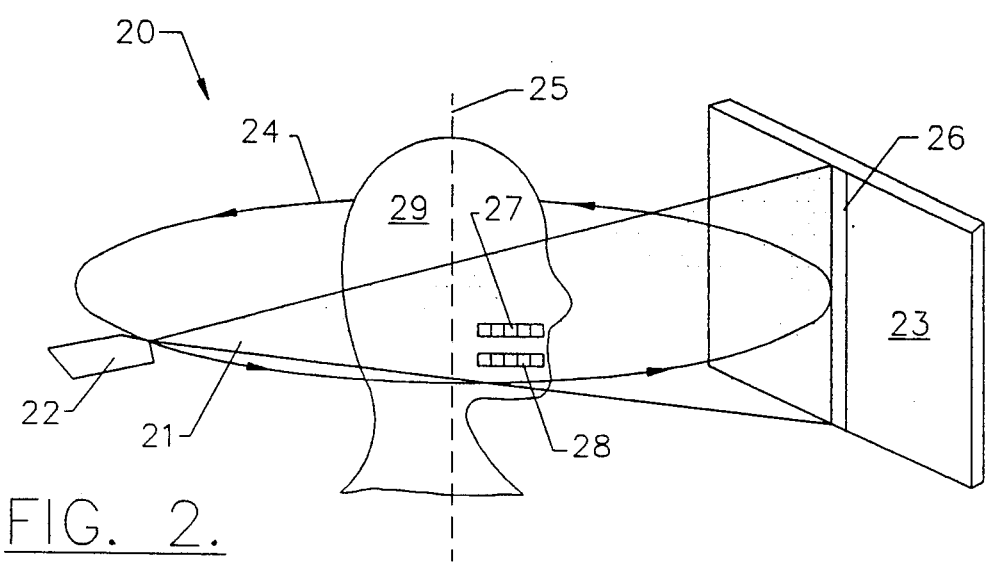
FIG. 2 schematically illustrates a conventional panoramic dental radiography system.

Referring now to FIG. 2, a schematic illustration of a panoramic radiography system is shown. System 20 includes an x-ray source 22 which projects a single, vertical, fan-shaped x-ray beam 21 onto an x-ray film 23. A slit collimator 26 may be used to reduce the effects of unwanted radiation. The source 22 and film 23 are rotated about horizontal rotation path 24 centered about a moving vertical axis 25, typically located anterior to typically the spine of the subject 29. In contrast with the tomosynthetic system of FIG. 1, there is relative motion between the source 22 and film 23. The relative motion is synchronized with the rotational movement of the source 22 and film 23 about axis 25. Accordingly, an extended film 23 is swept with a modulated fan-shaped beam to produce an extended image with a lateral extent and projective attributes impossible to produce directly from a single exposure.

Although the system of FIG. 2 is widely used for panoramic dental radiography, it has been found that this system is highly sensitive to subject positioning. Also, the beam passes through the subject's spine, which contributes to the x-ray dose so that it is higher than would ordinarily be required for imaging the teeth and jaw. Moreover, the spine creates a blurred artifact on the panoramic image which often interferes with proper diagnosis.

In the description of FIGS. 1 and 2, and the description of the invention to follow, the terms "horizontal" and "vertical" are referenced to an upright (sitting Or standing) subject 19, 29. In an upright subject, the systems 10, 20 are rotated horizontally, with beam 11 being a horizontal fan-shaped beam and beam 21 being a vertical fan-shaped beam. However, it will be understood by those having skill in the art that the terms "horizontal" and "vertical" are generally defined relative to the plane of the teeth, which is formed by the intersection of the upper row of teeth 17, 27 and the lower row of teeth 18, 28, and which is parallel to the bottom of the jaw. A direction parallel to the plane of the teeth is referred to as "horizontal" and a direction which is orthogonal to the plane of the teeth will be referred to as "vertical" in this description.

Figure 3:
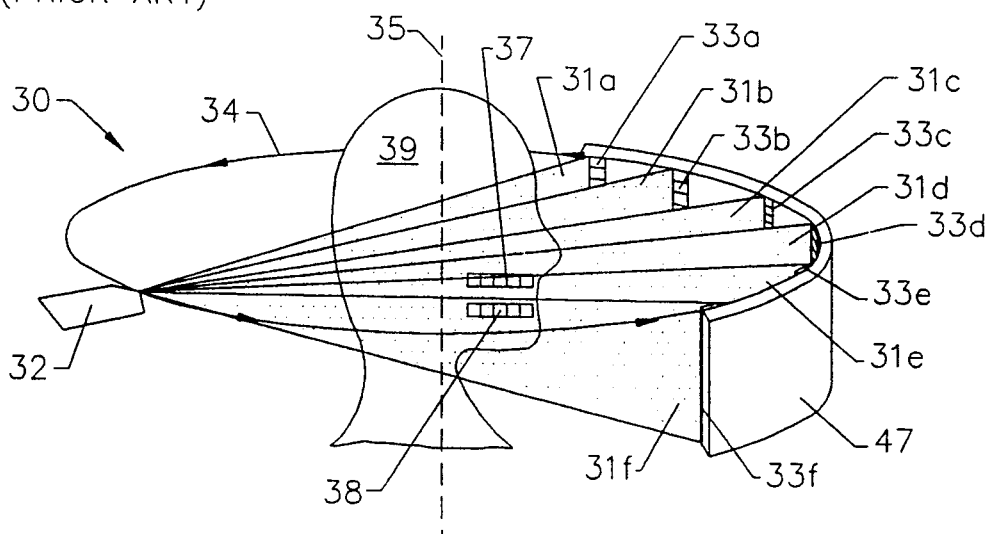
FIG. 3 schematically illustrates a tomosynthetic panoramic dental radiography system according to the present invention.

Referring now to FIG. 3, the panoramic dental radiography system of the present invention will now be described. As shown in FIG. 3, panoramic radiography system 30 includes a plurality, here six, of vertical (orthogonal to the plane of the teeth) fan-shaped diverging beams 31a-31f, produced by a source 32. The beams 31 may be produced from a single source 32 using a six-way collimator, as is well known to those having skill in the art. As also shown in FIG. 3, a vertical detector array having a plurality, here six, of linear detectors 33a-33f, is positioned so that a respective one of the beams 31 impinges on a respective one of the detectors 33 after passing through the subject 39. For reference purposes, upper and lower rows of teeth 37 and 38 are also shown. As also shown, source 32 and detector 33 are rotated in a horizontal rotation path 34, about a vertical axis 35 which may run through the subject's spine.

The system of FIG. 3 may be viewed as having a very narrow fan beam, resulting in a relatively wide region of sharp focus, so as to preclude significant blurring of malpositioned structures of diagnostic interest. Multiple exposures are taken at carefully selected angles, so that all areas of diagnostic interest are seen, and not obscured by superimposed images of irrelevant tissues in at least one projection. This results in a system that is characterized by multiple panoramic scans, each involving a different projection angle, to yield multiple, discrete, asymmetrical panoramic projections. By keeping track of the angles responsible for the resulting projections relative to the position of the subject, it is possible to tomosynthetically synthesize the resulting two-dimensional projections into a true three-dimensional representation of the tissues.

Figure 4:
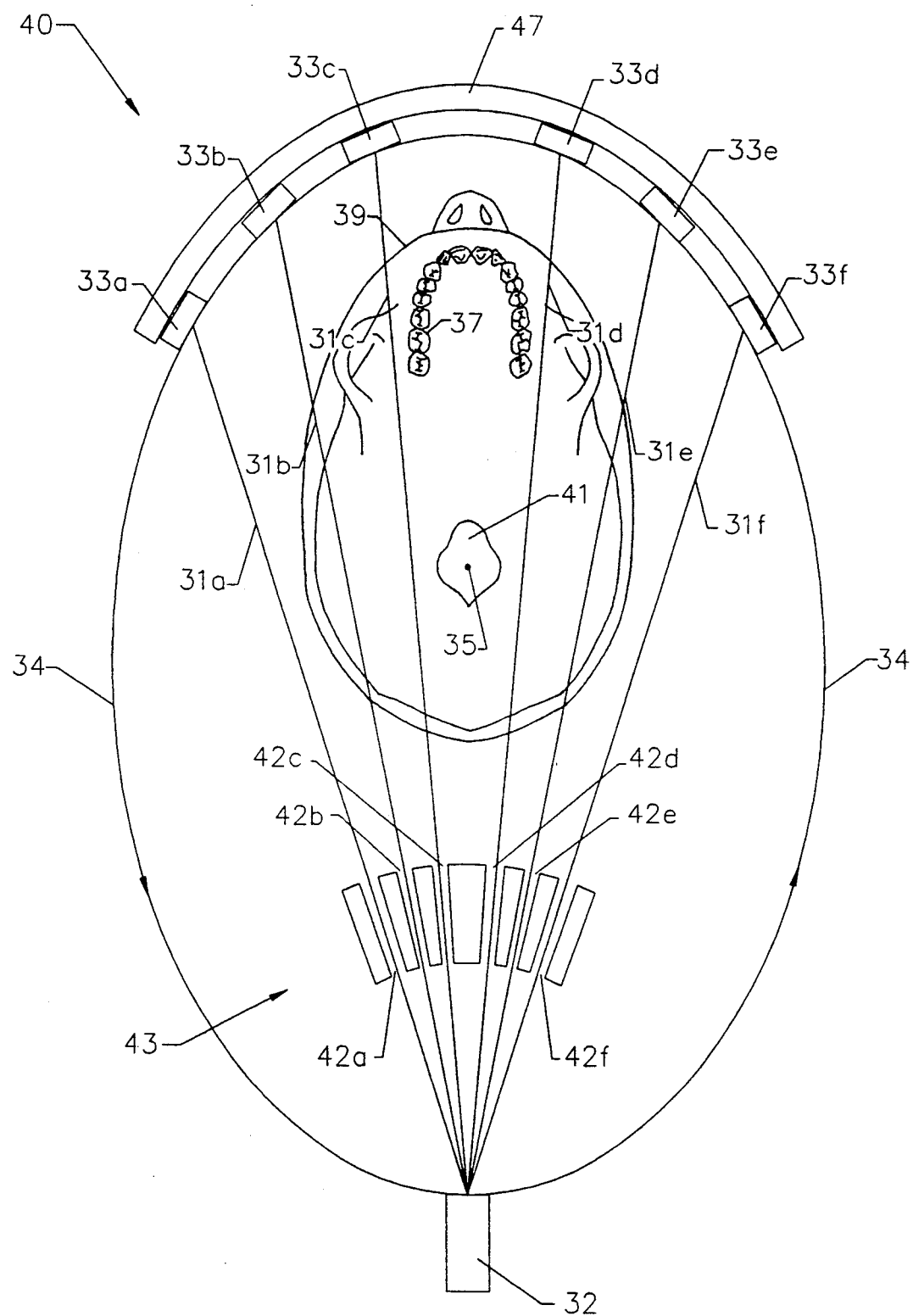
FIG. 4 schematically illustrates a cross sectional view of the tomosynthetic panoramic dental radiography system of FIG. 3 taken through the plane of the teeth.

Referring now to FIG. 4, a cross-sectional view of FIG. 3 taken through the plane of the teeth is shown. FIG. 4 illustrates that all of the beams 31a-31f are projected on either side of the spine 41, throughout the 360° rotation of the system around the subject. In particular, beams 31a-31c are on one side of the spine 41 and beams 31d-31f are on the opposite side of the spine 41 The spine is thereby minimally exposed to x-rays and the spine cannot act as a source for blurring the resulting image. As an example of the geometry of FIG. 4, beams 31a-31f may be spaced about the centerline in increments of 6, 10 and 16 degrees respectively, with the length of each beam being approximately 40 inches, and the distance from source 32 to center axis 35 being approximately 20 inches. Axis 35 may coincide with the center of spine 41 or may be placed between spine 41 and teeth 37.

The signals produced by detector arrays 33a-33f may be processed tomosynthetically. However, in contrast with conventional tomosynthesis, the multiple discrete angular projections required for panoramic tomosynthetic reconstruction are generated simultaneously rather than serially. This is accomplished through the use of multiple fan-shaped x-ray beams, each exposing the tissues from a different direction as the single x-ray source and multiple detector system rotates about a fixed or moveable center.

The present invention produces a number of advantages over known panoramic dental radiography systems. The x-rays can completely avoid the spine, so that no primary radiation reaches the radiosensitive marrow space in the spine. Moreover, projective artifacts of the spine do not find their way into the multiple panoramic images which are produced. Finally, the dose may be reduced because the x-rays are not directed through the spine.

The present invention also can differentially weight the dose distribution in the head so that it is concentrated in the tissues of diagnostic interest. For example, referring again to FIG. 4, the disk shaped region defined by the sector between beams 31c and 31d, as they rotate over 360°, is not exposed to any radiation dosage. The annular region between beams 31b and 31c (and 31d and 31e) is exposed to two beams as these beams rotate. The annular region between beams 31a and 31b (and beams 31e and 31f) is exposed to four beams. The remaining annular region is exposed to a total of six beams. Accordingly, the system tends to reduce and equalize the maximum intensity distribution of the x-rays.

The present invention produces multiple projections, at least one of which is likely to open most of the points of interproximal contact between the teeth. As is well known to those having skill in the art, it is desirable for a radiography system to allow points of interproximal contact between the teeth to be accurately viewed.

The panoramic image may be obtained by the present invention without the precise subject placement heretofore required. Finally, since theory and existing software have demonstrated that tomosynthetic data can be processed into any desired two-dimensional projection, tissue changes can be quantitatively obtained from careful comparison of existing panoramic radiographs and those produced according to the present invention.

The present invention can utilize well known commercially available components to achieve improved results. In particular, a conventional source 32 such as contained on a model Panex-E1 machine, marketed by Morita Corporation, and a customized multi-slit collimator may be used to produce the multiple vertical fan-shaped beams. A plurality of detectors, such as six model THX 1089 linear x-ray detectors, marketed by Thompson CSF, may be used to detect the radiation. This device is a 4¼ inch linear array of 1000 CCD elements.

In contrast with conventional radiography of FIG. 2, relative movement between detectors 33 and source 32 is not necessary, so that mechanical synchronization is not required. The signals from the detectors 33 may be processed using conventional tomographic processing steps, so that new processing algorithms need not be developed, and known tomosynthetic enhancement techniques may be used. For example, Computer correction of artifacts such as variations in contrast and differential magnifications, and computer pattern recognition techniques may be used. The electronic images produced may be transmitted from one computer to another, facilitating communications for diagnostic and forensic purposes.

Figure 5:
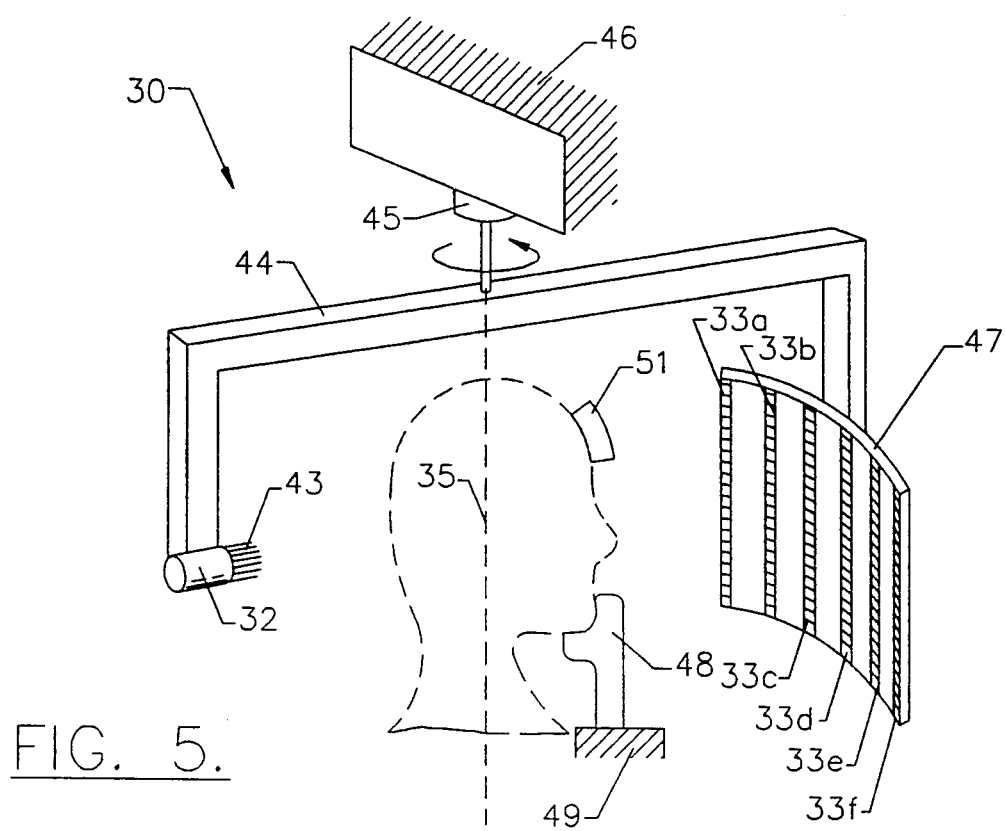
FIG. 5 schematically illustrates the mechanical configuration of the system of FIG. 3.

Referring now to FIG. 5, a simplified schematic illustration of the mechanical configuration of the system 30 of the present invention will now be described. As shown, x-ray source 32 and collimator 43 are carried at one end of support arm 44, with the detectors 33a–33f being mounted at the other end thereof. The detectors 33 may be mounted on a detector support 47. As shown, arm 44 is mounted for horizontal movement about axis 35 using a motor 45 which is mounted on support member 46.

Apparatus 30 also includes subject positioning means, for positioning the subject relative to the source 32 and detector array 33 to obtain the geometric relationship described in connection with FIGS. 3 and 4. The subject support may include a jaw support 48 mounted on a base 49, and may also include an optional skull support 51. The supports 48 and 51 are preferably adjustable, to permit precise positioning of a subject's head 39 relative to the apparatus 30. The detailed mechanical design may be based upon known panoramic dental x-ray systems, and need not be described herein further. For example, a Panex-E machine, marketed by J. Morita Corp., Tustin, Calif., may be modified.

Figure 6A:
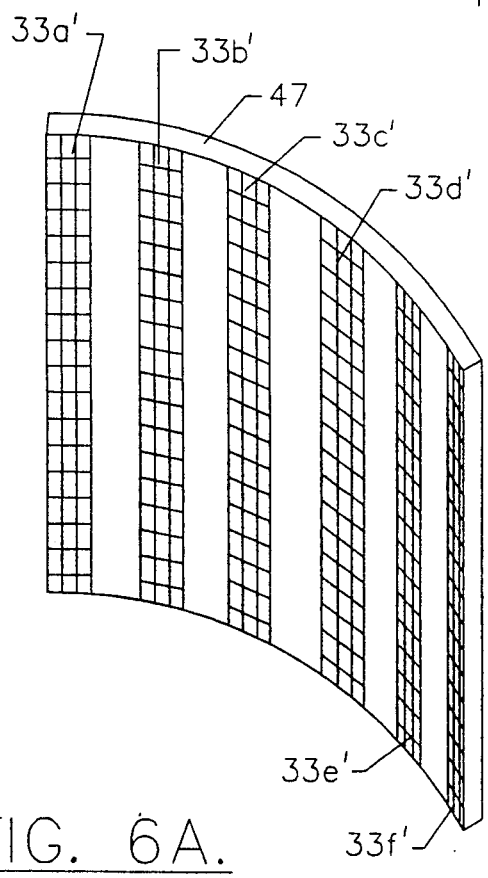
FIGS. 6A and 6B illustrate alternate configurations for the detector arrays of the system of FIG. 3.
Figure 6B:
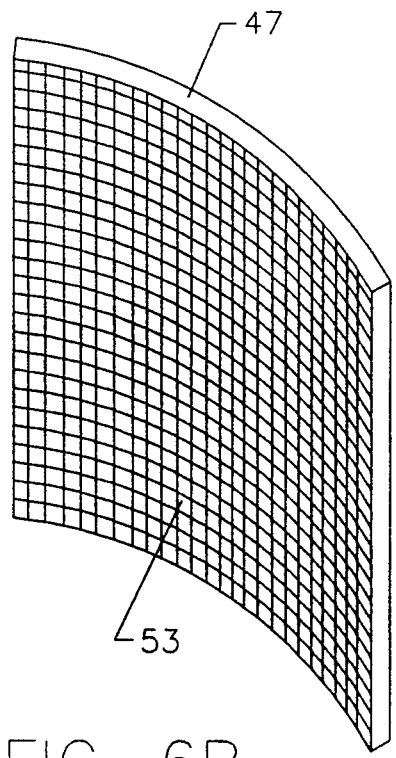

Referring now to FIGS. 6A and 6B, alternate embodiments for the detectors of FIG. 5 are shown. FIG. 6A illustrates four detector arrays 33a'–33d' each of which include a plurality (such as three) of rows of CCDs. The two-dimensional detector arrays 33' may encompass the full extent of a widened but still collimated fan-shaped beam. Accordingly, the number of independent projection angles for tomosynthetic reconstruction may be multiplied by the number of rows of CCDs. The array of FIG. 6A increases the flexibility of the system, which may permit tailoring the projection geometry to a specific imaging task. For example, a hybrid system may be generated which anisotropically samples both at low and at high angular resolutions depending on the importance of the structures passing through the fan-shaped beams at specific rotational angles. FIG. 6B illustrates a single large two-dimensional matrix of detector elements 53, which provides the ultimate in flexibility.

Figure 7:
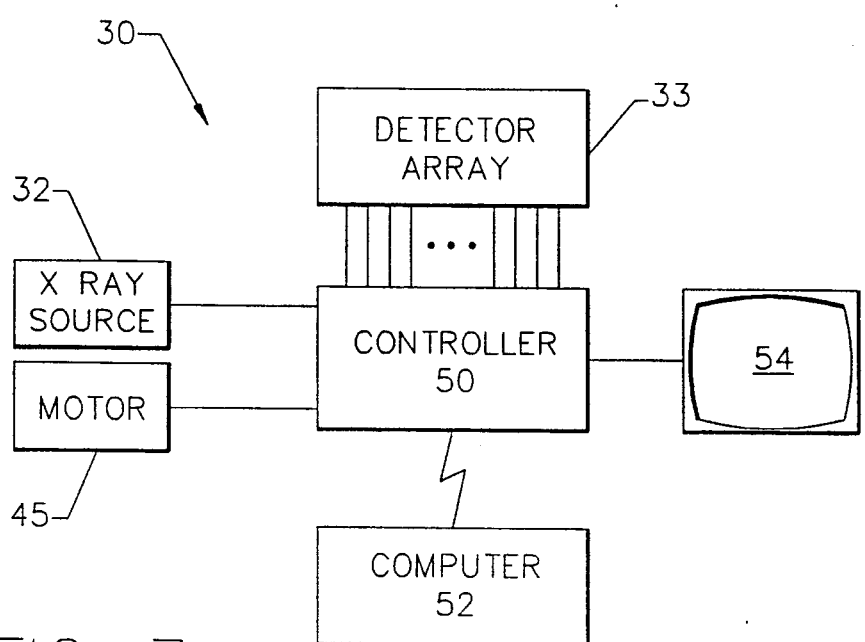
FIG. 7 illustrates a general electrical schematic diagram of the system of FIG. 3.

Referring now to FIG. 7, a general hardware block diagram of the apparatus 30 of the present invention will now be described. As shown, an electronic controller such as a stored program microcomputer may be electrically connected to x-ray source 32, motor 45 and detector array 33, for electronically controlling x-ray generation by x-ray source 32, and the rotation of motor 45. The signals from the detector array 33 may be stored in controller 50 and may be processed therein as described below in connection with FIG. 8. The processed signals may be transferred to a remote computer 52 for remote analysis or viewing. The image may also be projected onto a visual display 54 such as a cathode ray tube (CRT) screen. The manner of connecting the elements of FIG. 7 are well known to those having skill in the art and need not be described in further detail herein.

Figure 8:
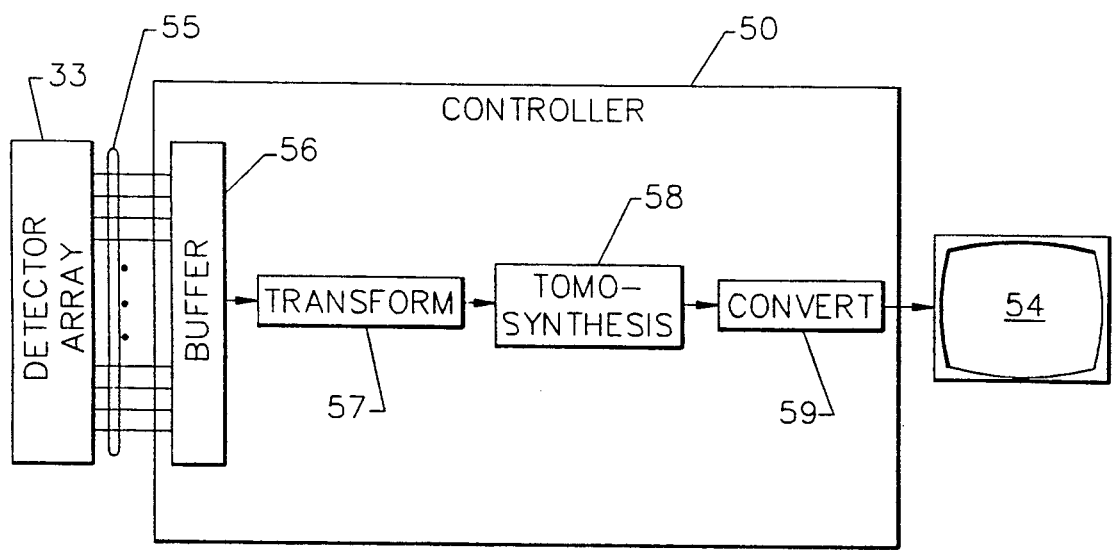
FIG. 8 illustrates a more detailed electrical schematic diagram of the electronic controller of FIG. 7.

Referring now to FIG. 8, a detailed description of controller 50 will now be described. As shown, a plurality of signal lines 55 may connect detector array 33 to a buffer 56 in controller 50, to allow high speed parallel transmission of data. Alternatively, serial transmission over fewer lines may be provided. It will also be understood by those having skill in the art that less than all of the linear arrays may be activated during a given scan, so that the depth of field around the focal plane may be altered during the process of data acquisition. This decreases the required frame buffer size, and the required data transfer rates.

After appropriate storage of the signals in the buffer 56, a nonlinear transformation may be applied by transforming means 57 in order to convert the curved detector geometry of FIG. 3 into the equivalent of the flat detector geometry of FIG. 1. Alternatively, this transformation need not be performed, and the data produced by the geometry of FIG. 3 may be directly processed tomosynthetically, as described below. Conventional tomosynthetic processing means 58 may be used to synthesize tomosynthetic slices. A conventional display converter may be used to convert the tomosynthetic signals into a format for display on display 54. The design of these elements are well known to those having skill in the art and need not be described herein further.

Figure 9A:
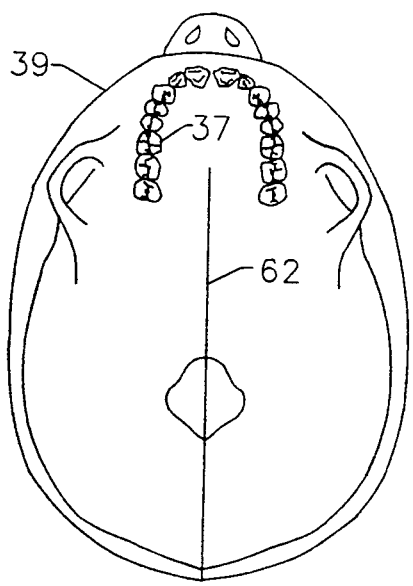
FIGS. 9A-9C illustrate the theoretical morphological transformation of a subject's head during panoramic radiographic operations.
Figure 9B:
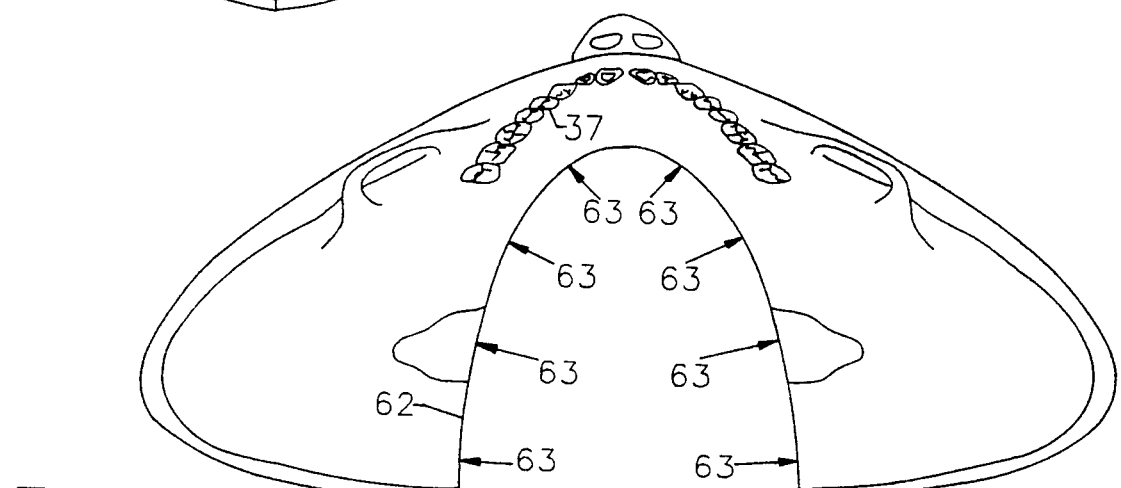
Figure 9C:
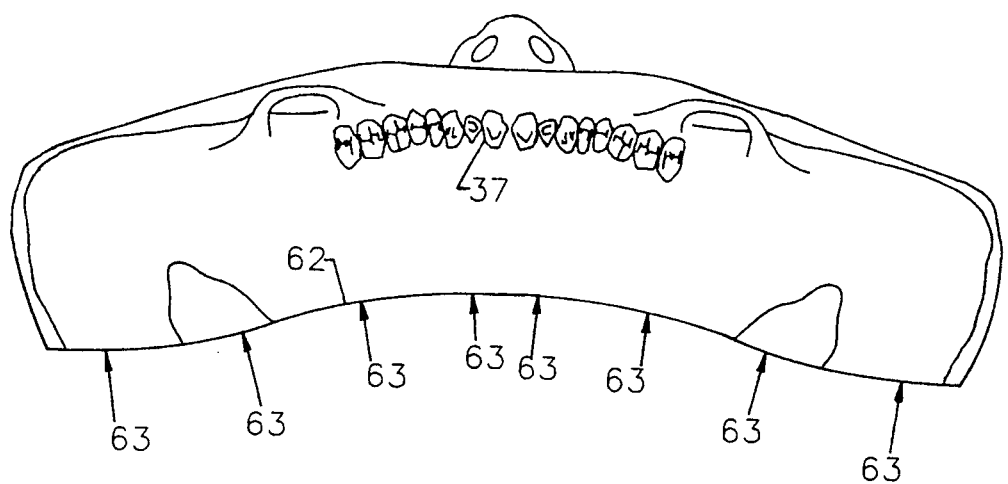

The data produced by the geometry of FIG. 3 may be directly processed tomosynthetically because the projection process responsible for conventional panoramic imaging is the conceptual equivalent of applying a morphological transformation to the actual head of the subject and then irradiating the resulting grossly distorted tissue mass with parallel collimated x-rays as might be produced from a conventional x-ray machine FIGS. 9A–9C illustrate schematically how the head 39 might be cut along line 62, and stretched to achieve this result. The arrows 63 indicate the direction of the warping displacements and they also approximate the altered direction of the x-radiation as it passes through the tissues. In the limit, the arrows 63 become parallel, suggesting that a conventional fixed transmission radiograph of the distorted tissue mass would produce the equivalent of a conventional panoramic radiograph.

Figure 10A:
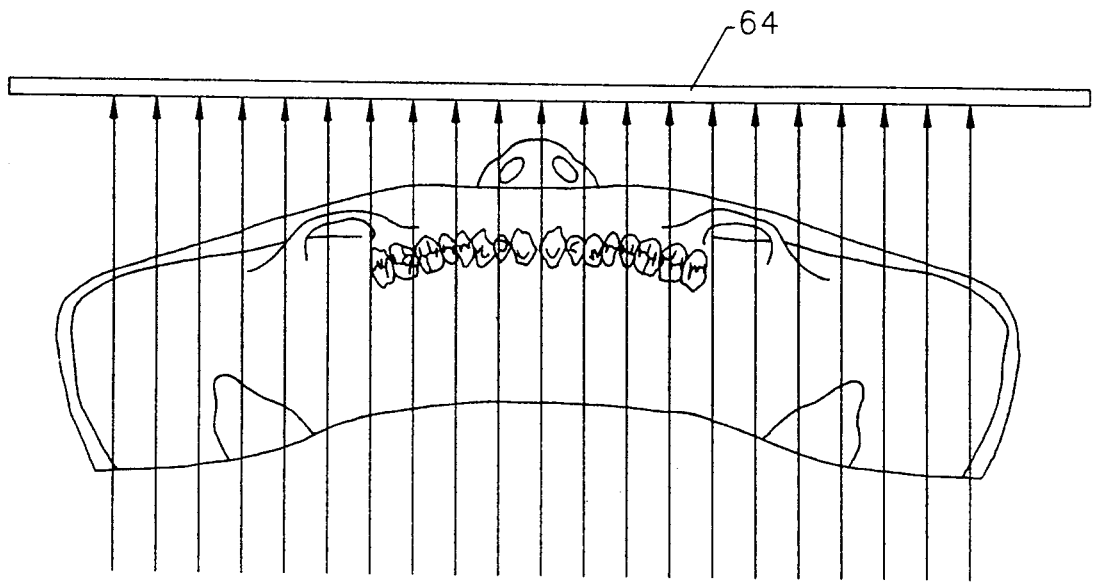
FIGS. 10A and 10B illustrate irradiation of the morphologically transformed head of FIG. 9C during conventional panoramic radiography and during panoramic tomosynthesis underlying the present invention.
Figure 10B:
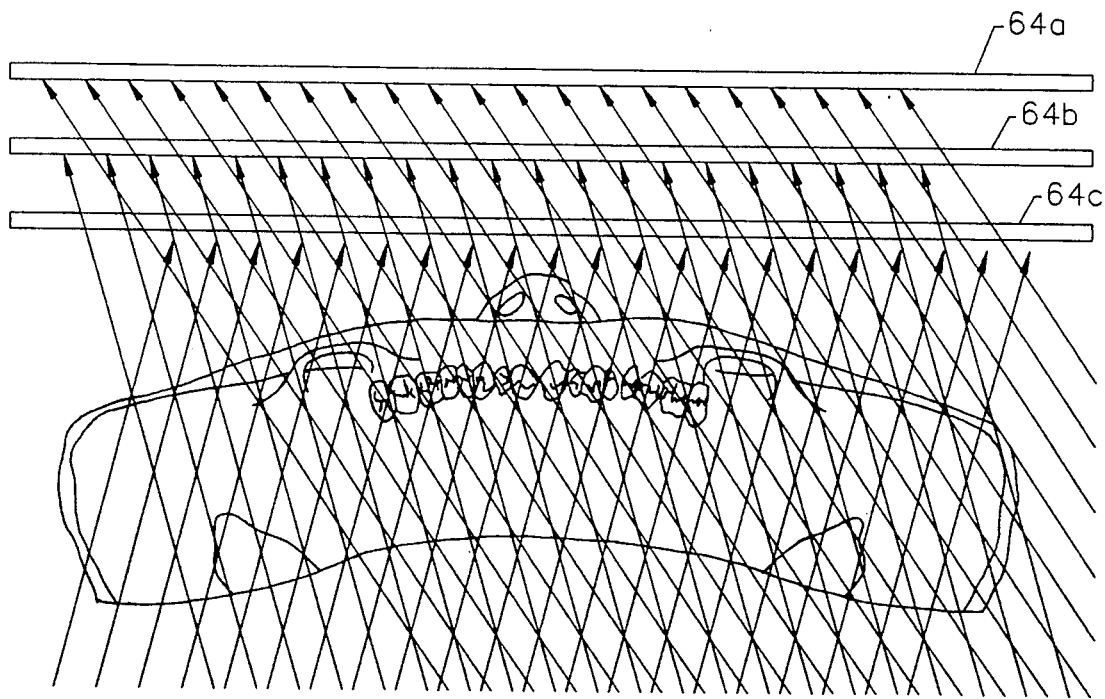

Referring to FIG. 10, instead of irradiating the distorted tissue mass with a single beam of collimated x-rays coming from a single source as shown in FIG. 10A, the distorted tissue mass is irradiated with multiple beams directed from multiple angles in such a way that each projection is produced independently from the others, as shown for three arbitrary angles in FIG. 10B. The resulting projections on x-ray films labeled 64a, 64b and 64c may be considered to be the equivalent of three (or any reasonable number) tomosynthetic component projections so produced that need only be shifted laterally and added together to yield tomosynthetic slices which would parallel the film planes in this conceptual simulation, and which would pass through any desired depth in the distorted tissue mass. The multiple fan beams of the present invention, achieve this effect simultaneously while the panoramic sweep is performed. The result is hybrid tomosynthetic component projections that may be shifted and added to yield slices which when related to the undistorted head are of nonuniform thickness and are curved in a pattern which parallels the dental arch in the region of the teeth.

Figure 11:
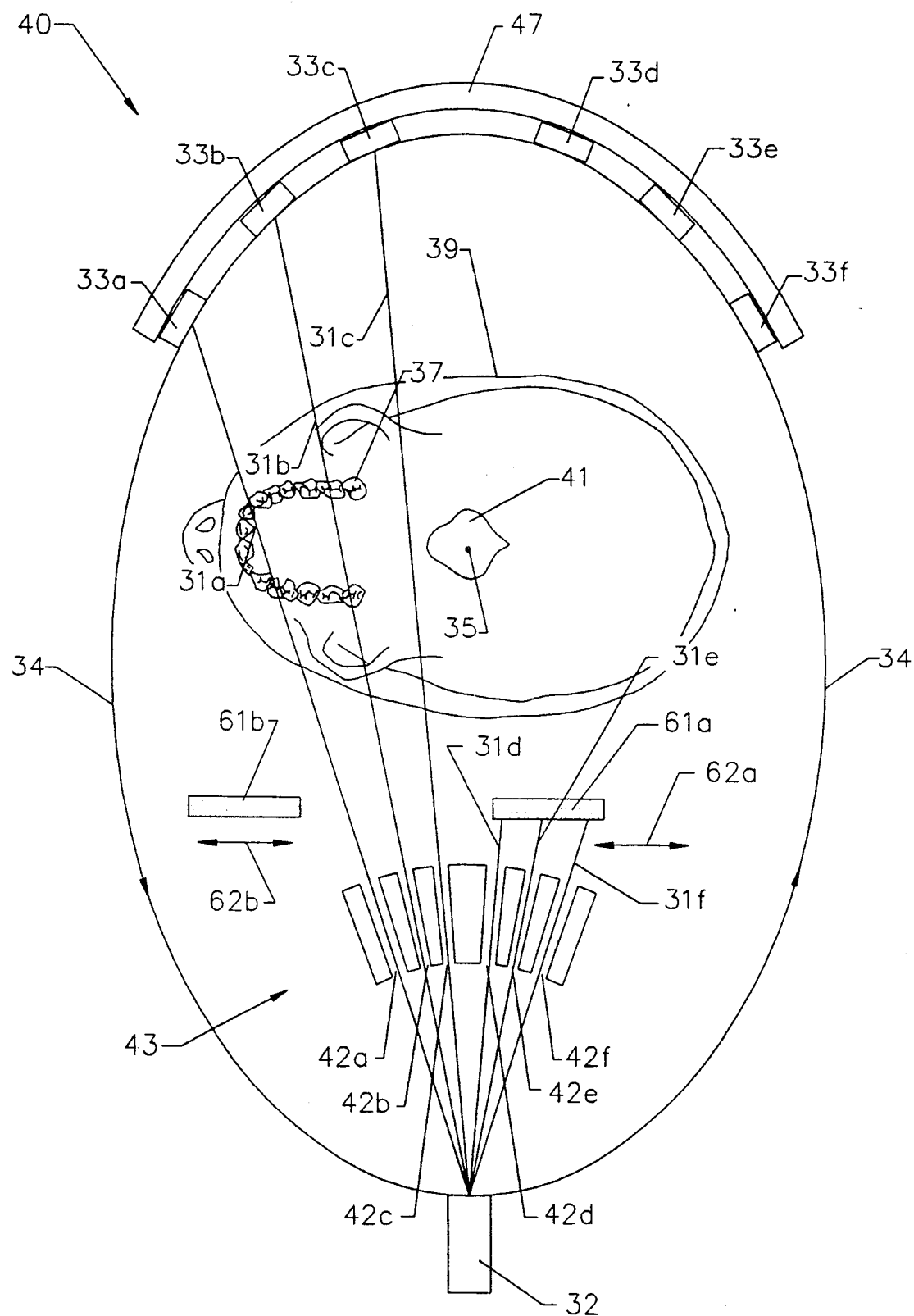
FIG. 11 illustrates a general schematic diagram of an alternative embodiment of a panoramic dental radiography system of the present invention.

Referring now to FIG. 11, an additional aspect of the present invention is illustrated. FIG. 9 illustrates the same geometrical projection as FIG. 4, except that the apparatus has rotated 90° clockwise. In this position, half the beams 31d, 31e, and 31f pass through an area of no dental interest. Accordingly, to minimize the subject's radiographic dosage, at least one of the beams are suppressed during a portion of the rotation thereof. In particular, a shield 61a is provided to block beams 31d, 31e and 31f in synchronism with the rotation of the apparatus. Similarly, a shield 61b may be provided to block beams 31a, 31b and 31c at the appropriate times during the rotation. Shields 61a-61b may be moved in the direction shown by arrows 62a, 62b, to block one or more of the fan-shaped beams 31 when they are not imaging an area of interest. Dosage is thereby reduced further without reducing the quality or resolution of the radiographic image. It will be understood by those having skill in the art that the beams may also be individually turned off at various rotational positions, rather than blocked, to suppress the beams and achieve lower subject dosage.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A dental radiography system comprising:
radiographic source means, for simultaneously projecting a plurality of diverging, fan-shaped radiation beams through a subject's teeth, each fan-shaped beam lying in a plane which is orthogonal to the plane of the teeth, with each fan-shaped beam avoiding the subject's spine;
radiographic detecting means, for detecting attenuated radiation which emerges through the teeth, the detected attenuated radiation being free of attenuation produced by the subject's spine; and
means for synchronously rotating said radiographic source means and said radiographic detecting means about an axis which is orthogonal to the plane of the teeth, each of said fan-shaped beams avoiding the subject's spine during rotation thereof, such that the detected attenuated radiation produces a panoramic image of the teeth, which is free of image artifacts produced by irradiation of the spine.

2. The dental radiography system of claim 1 wherein said plurality of diverging, fan-shaped beams are symmetrically projected about the subject's spine, and wherein each of said fan-shaped beams avoids the subject's spine.

3. The dental radiography system of claim 1 further comprising means for positioning a subject's head such that said plurality of diverging fan-shaped beams pass through the subject's teeth, lie in a plane which is orthogonal to the plane of the subject's teeth, and avoid the subject's spine, and said radiographic source means and said radiographic detecting means synchronously rotate on opposite sides of the subject's head, about an axis which is orthogonal to the plane of the subject's teeth, with each of said fan-shaped beams avoiding the subject's spine during rotation thereof, such that the detected radiation produces a panoramic image of the subject's teeth which is free of image artifacts produced by irradiation of the spine.

4. The dental radiography system of claim 1 wherein said radiographic detecting means comprises a like plurality of linear radiation detectors, orthogonal to the plane of the teeth, a respective one of which is positioned to intercept a respective one of the fan-shaped beams which emerge through the teeth, free of attenuation produced by the subject's spine.

5. The dental radiography system of claim 4 wherein each linear radiation detector comprises a linear array of solid state detectors, arranged in a single row orthogonal to the plane of the teeth.

6. The dental radiography system of claim 4 wherein each linear radiation detector comprises a linear array of solid state detectors, arranged in a plurality of rows orthogonal to the plane of the teeth.

7. The dental radiography system of claim 1 wherein said radiographic detecting means comprises a two-dimensional array of solid state detectors, for intercepting all of said fan-shaped beams which emerge through the teeth, free of attenuation produced by the subject's spine.

8. The dental radiography system of claim 1 wherein said synchronous rotating means comprises means for synchronously rotating said radiographic source means and said radiographic detecting means about an axis which is orthogonal to the plane of the teeth and passes through the subject's spine.

9. The dental radiography system of claim 1 further comprising electronic controlling means, electrically connected to said radiographic detecting means, for producing a representation of a panoramic dental image from the detected attenuated radiation which emerges through the teeth.

10. The dental radiography system of claim 1 wherein at least one of said fan-shaped beams fails to pass through the teeth during a portion of its rotation about said axis, said dental radiography system further comprising means for selectively suppressing said at least one of said radiation beams during said portion of rotation thereof, to reduce the subject's radiation dosage.

11. The dental radiography system of claim 10 wherein said selective suppressing means comprises a moveable radiation shield, for selectively blocking said at least one of said radiation beams during said portion of rotation thereof.

12. A dental radiography method comprising the steps of:
   simultaneously projecting a plurality of diverging, fan-shaped radiation beams through a subject's teeth, each fan-shaped beam lying in a plane which is orthogonal to the plane of the teeth and avoiding the subject's spine;
   rotating said plurality of diverging, fan-shaped radiation beams about an axis which is orthogonal to the plane of the teeth, each of said fan-shaped beams avoiding the subject's spine during rotation thereof; and
   detecting attenuated radiation which emerges through the teeth, the detected attenuated radiation being free of attenuation produced by the subject's spine, to produce a panoramic image of the teeth which is free of image artifacts produced by irradiation of the spine.

13. The dental radiography method of claim 12 wherein said simultaneously projecting step comprises the step of symmetrically projecting the plurality of diverging, fan-shaped beams about the subject's spine, with each of said fan-shaped beams avoiding the subject's spine.

14. The dental radiography method of claim 12 wherein said detecting step comprises the step of individually detecting each of said plurality of fan-shaped radiation beams at an individual radiation detector.

15. The dental radiography method of claim 12 wherein said rotating step comprises the step of rotating said radiographic beams about an axis which is orthogonal to the plane of the teeth and passes through the subject's spine.

16. The dental radiography method of claim 12 further comprising the step of producing a representation of a panoramic dental image from the detected attenuated radiation which emerges through the teeth, free of attenuation produced by the subject's spine.

17. The dental radiography method of claim 12 wherein at least one of said fan-shaped beams fails to pass through the teeth during a portion of its rotation about said axis, said method further comprising the step of selectively suppressing said at least one of said radiation beams during said portion of rotation thereof, to reduce the subject's radiation dosage.

18. The dental radiography method of claim 17 wherein said selective suppressing step comprises the step of selectively blocking said at least one of said radiation beams during said portion of rotation thereof.

* * * * *